United States Patent
Zemlan et al.

(10) Patent No.: US 6,797,478 B1
(45) Date of Patent: Sep. 28, 2004

(54) METHOD OF DETECTING AXONAL DAMAGE, FROM ASSOCIATED DISEASE STATES USING TAU MONOCLONAL ANTIBODIES

(75) Inventors: Frank P. Zemlan, Cincinnati, OH (US); Thomas A. Campbell, Massillon, OH (US)

(73) Assignee: University of Cincinnati, Cincinnati, OH (US)

( * ) Notice: Subject to any disclaimer, the term of this patent is extended or adjusted under 35 U.S.C. 154(b) by 0 days.

(21) Appl. No.: 09/035,708

(22) Filed: Mar. 5, 1998

(51) Int. Cl.[7] .................. G08N 33/53; G08N 33/577; G08N 33/68
(52) U.S. Cl. ................. 435/7.1; 435/7.92; 435/7.94
(58) Field of Search ................. 435/7.1, 7.92, 435/7.94

(56) References Cited

FOREIGN PATENT DOCUMENTS

| WO | WO 93/03369 | 2/1993 |
|---|---|---|
| WO | WO 93/08302 | 4/1993 |
| WO | WO 93/11231 | 6/1993 |
| WO | WO 94/13795 | 6/1994 |
| WO | WO 95/17429 | 6/1995 |
| WO | WO 96/04309 | 2/1996 |

OTHER PUBLICATIONS

Grysen et al. J. Molecular Recognition 1:32–41, 1988.*

* cited by examiner

*Primary Examiner*—Gary Kunz
*Assistant Examiner*—Robert C. Hayes
(74) *Attorney, Agent, or Firm*—Frost Brown Todd LLC

(57) ABSTRACT

Patients having several neurological diseases have been shown to have elevated levels of axonally-derived proteins (i.e. tau and neurofilament proteins) in cerebrospinal fluid (CSF) and in brain tissue. Three monoclonal antibodies (MAbs) recognizing CSF tau proteins were developed. The Mabs were found to label a ladder of 30 kD to 50 kD tau proteins in CSF from patients with disease states producing axonal damage such as head trauma or CNS tumor but not in CSF from controls. High levels of tau protein in CSF were shown to be diagnostic of axonal degeneration in head trauma. An ELISA assay was developed with these MAbs to aid in the diagnosis of patients with axonal damage.

9 Claims, 6 Drawing Sheets

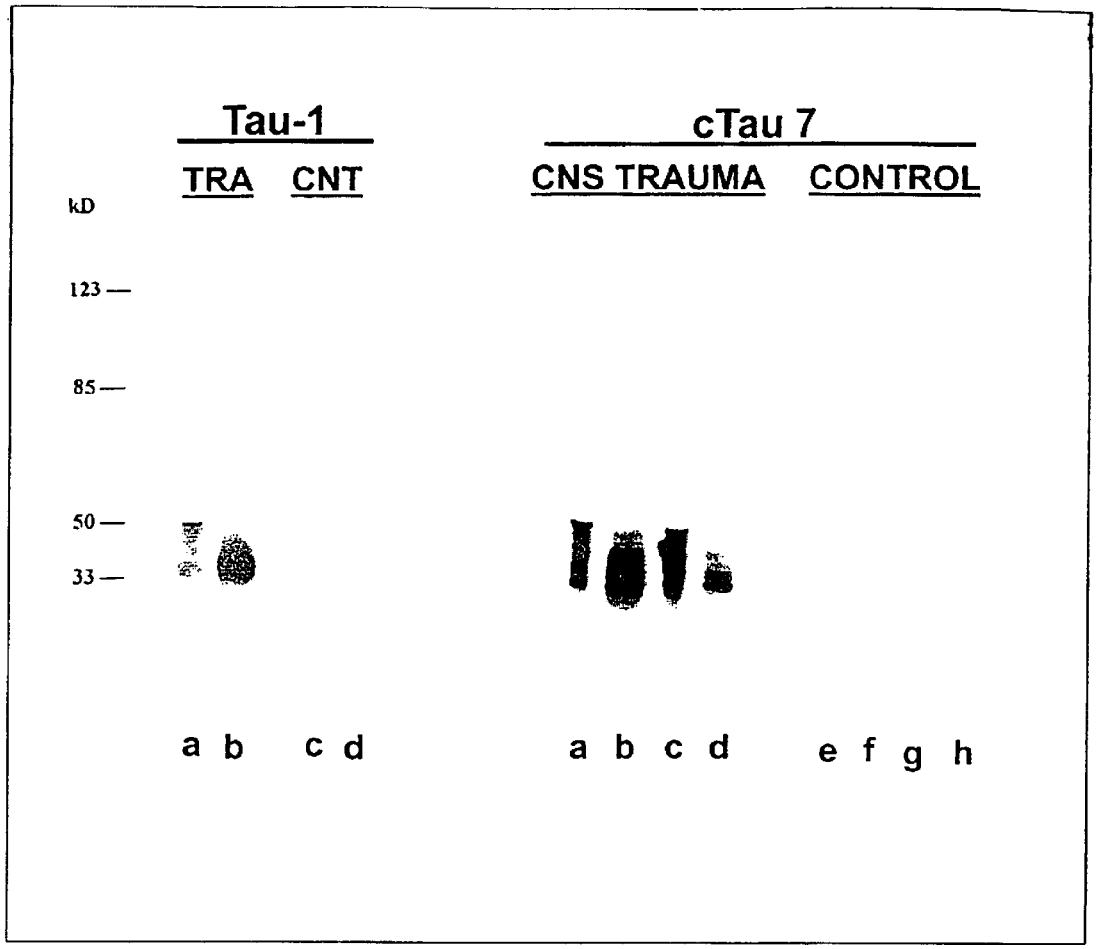

Fig. 1. Monoclonal antibodies recognizing cerebrospinal fluid cleaved tau proteins were developed by differential CSF screening. *Left panel:* Initial studies demonstrated that Mab Tau-1 labeled 30 kDa to 50 kDa CSF proteins in CNS trauma patients (TRA; lane a 50 μl CSF, lane b 10 μl CSF) but not normal controls (CNT; lane c and d both 50 μl CSF). *Right panel:* Mabs were developed that specifically recognized 30 kDa to 50 kDa CSF tau proteins employing a differential CSF screen. Hybridomas were selected that labeled CSF from CNS trauma patients (lanes a-d) but not control patients (lanes e-h). The same patient samples were run in lanes a and b in left and right panels. cTau7 lanes a and e-h 50 μl CSF, lanes b-d 10 μl CSF. Molecular weight markers shown at left.

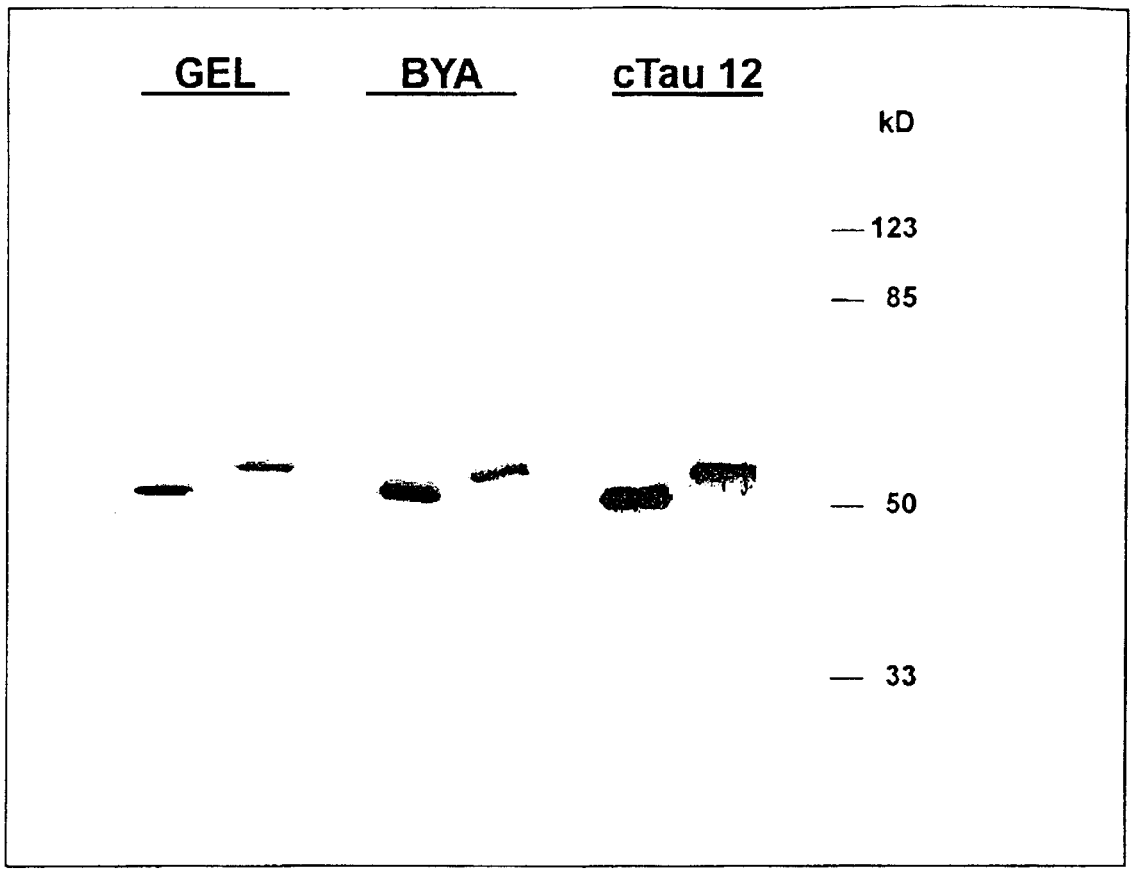
Fig. 2. CSF cleaved tau Mabs label recombinant tau. Commassie Blue stained 10% gel with recombinant 3-repeat tau (Gel, left lane, 1 μg) and 4-repeat tau (Gel, right lane, 1 μg). Recombinant tau blotted with BYA (0.07 μg/lane) and cTau12 (2.5 μg/lane). Molecular weight markers shown at right.

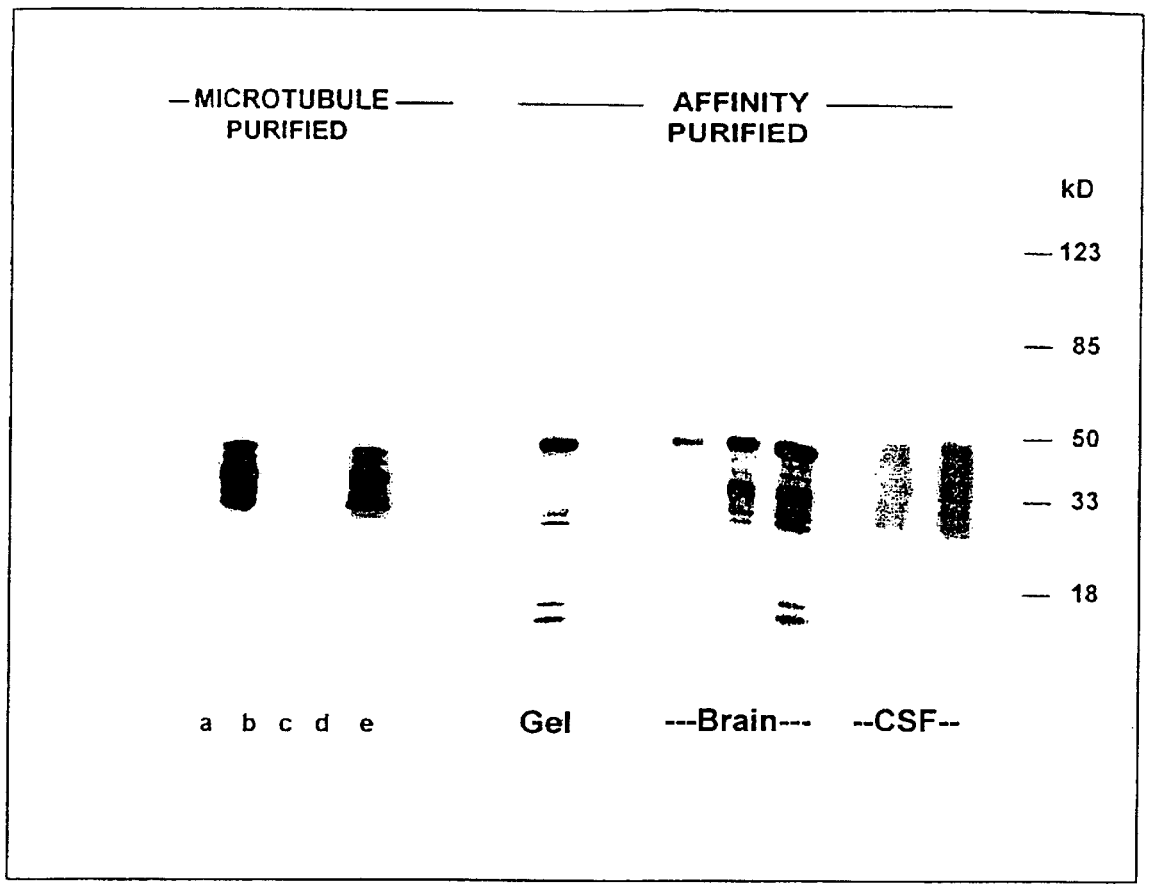

Fig. 3. CSF and brain cleaved tau proteins bind microtubules. *Microtubule Purified:* Initially, taxol polymerized microtubules were salt extracted to insure that no cTau7 immunoreactive proteins were present (lane a). Microtubules were then incubated with a preparation of CSF cleaved tau proteins (lane b, 1 µg) and washed several times until the supernatant was free of cTau7 reactivity (lanes c and d). Microtubule bound proteins were salt extracted yielding 30 kDa to 50 kDa cTau7-reactive cleaved tau proteins (lane e). Similar results were obtained with Mabs cTau8 and cTau12 (data not shown). *Affinity Purified:* cleaved tau proteins were affinity purified from either CSF or brain with Mabs cTau7, cTau8 and cTau12 coupled to Protein G agarose. Commassie Blue stained gels indicated that affinity purified cleaved tau consisted of a primary 50 kDa protein band (gel, 1 µg). Immunoblots of affinity purified CSF (100 and 500 ng) and brain (10, 30 and 100 ng) with cTau7 revealed 30 kDa to 50 kDa protein bands. Similar results were observed with Mabs cTau8 and cTau12 (data not shown). Position of molecular weight markers shown at right.

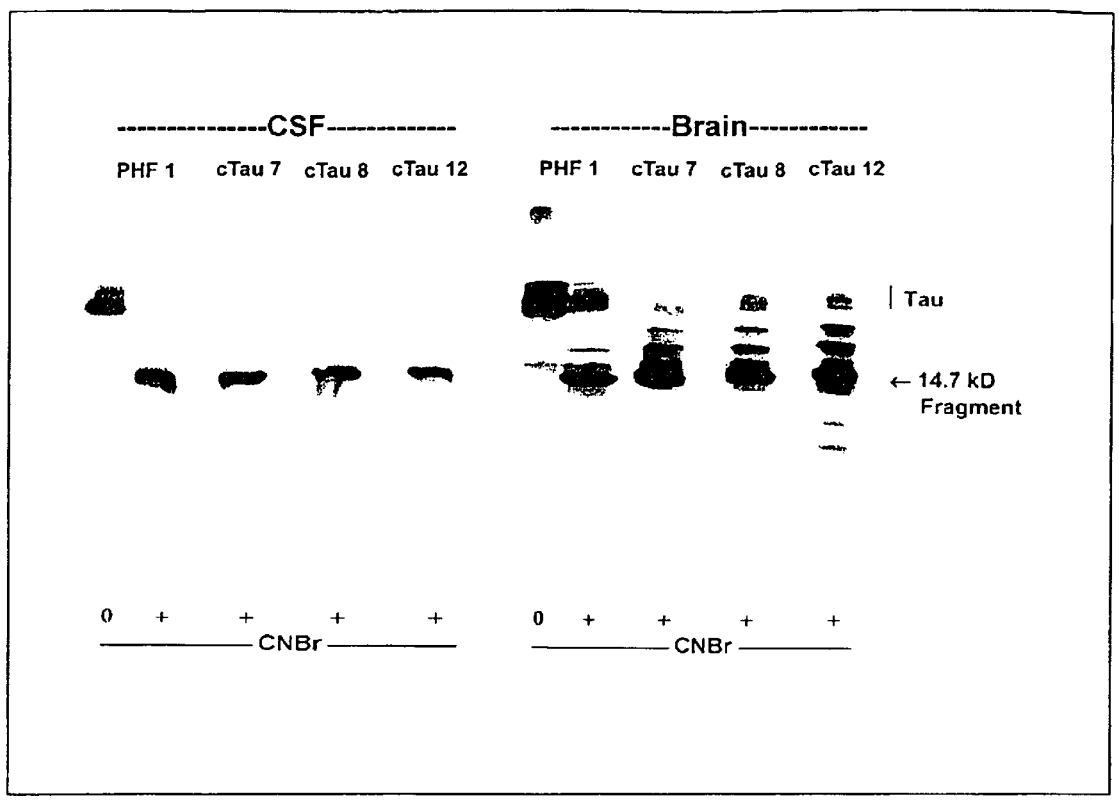

Fig. 4. Mabs cTau7, cTau8 and cTau12 recognize a 14.7 kDa CNBr digestion fragment occurring in patient CSF or brain. Cleaved tau from CSF or brain (2 μg/lane) was treated either with (+) or without (0) CNBr and blotted with Mabs PHF-1, cTau7, cTau8 and cTau12. All four antibodies appeared to predominantly label the same CNBr digestion fragment consisting of tau amino acids pro$^{251}$ to met$^{419}$. The PHF-1 fragment has a reported molecular weight of 14.7 kDa (Zemlan and Dean, 1996). Blots are from a single 15% gel. The position at which non-digested cleaved tau migrated is shown (Tau).

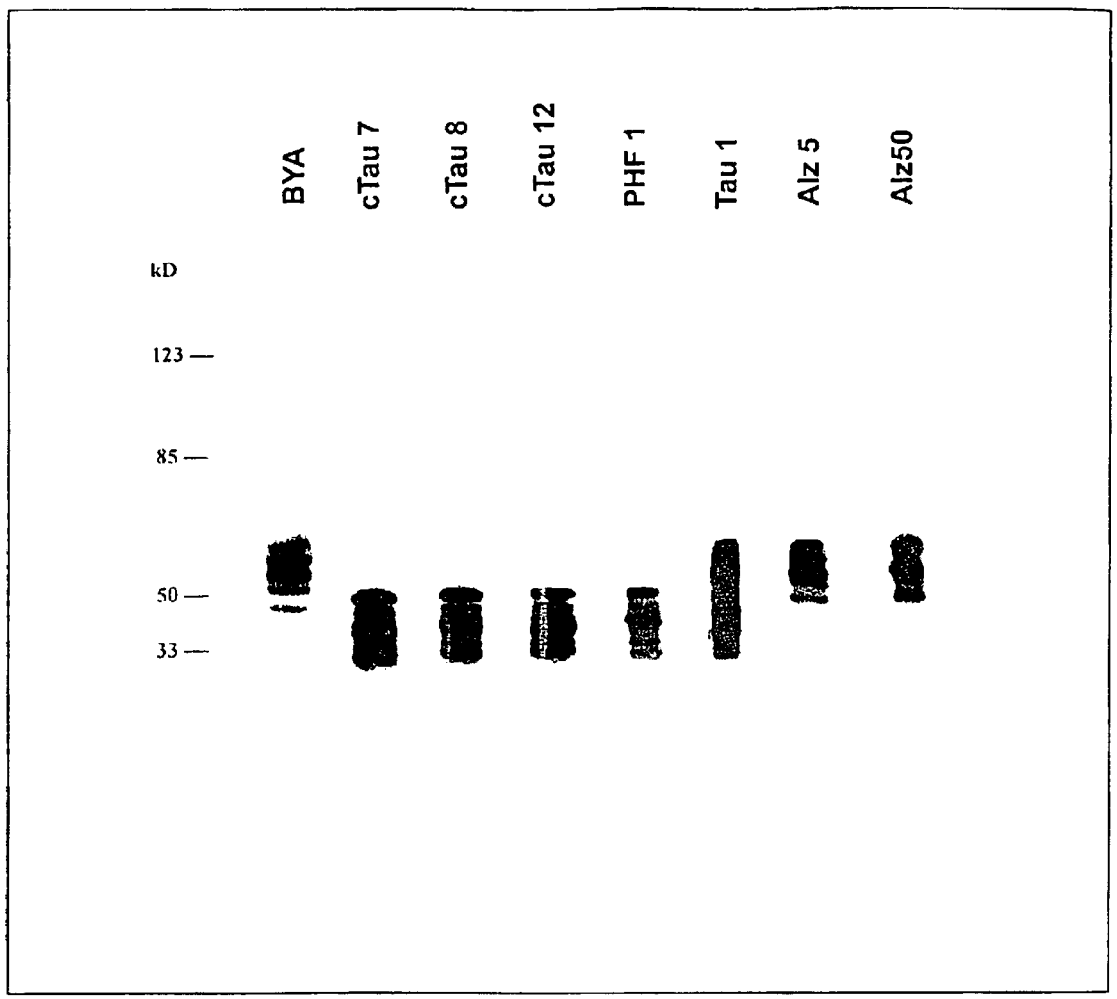

Fig. 5. *Post Mortem* brain contains both full length 48 kDa to 68 kDa tau proteins and 30 kDa to 50 kDa cleaved tau proteins. Intact tau proteins were selectively labeled with the tau antibody BYA, the C-terminal tau antibody Alz5 and the N-terminal tau antibody Alz50 in heat stable preparations of *post mortem* brain. Cleaved tau proteins were selectively labeled with Mabs cTau7, cTau8, cTau12 and PHF1 that recognizes phospho-ser$^{396}$ of tau. Mab Tau-1 that recognizes non-phosphorylated ser$^{199}$ of tau labeled both forms of tau. These data suggest that tau is cleaved and phosphorylated at ser$^{396}$ in brain.

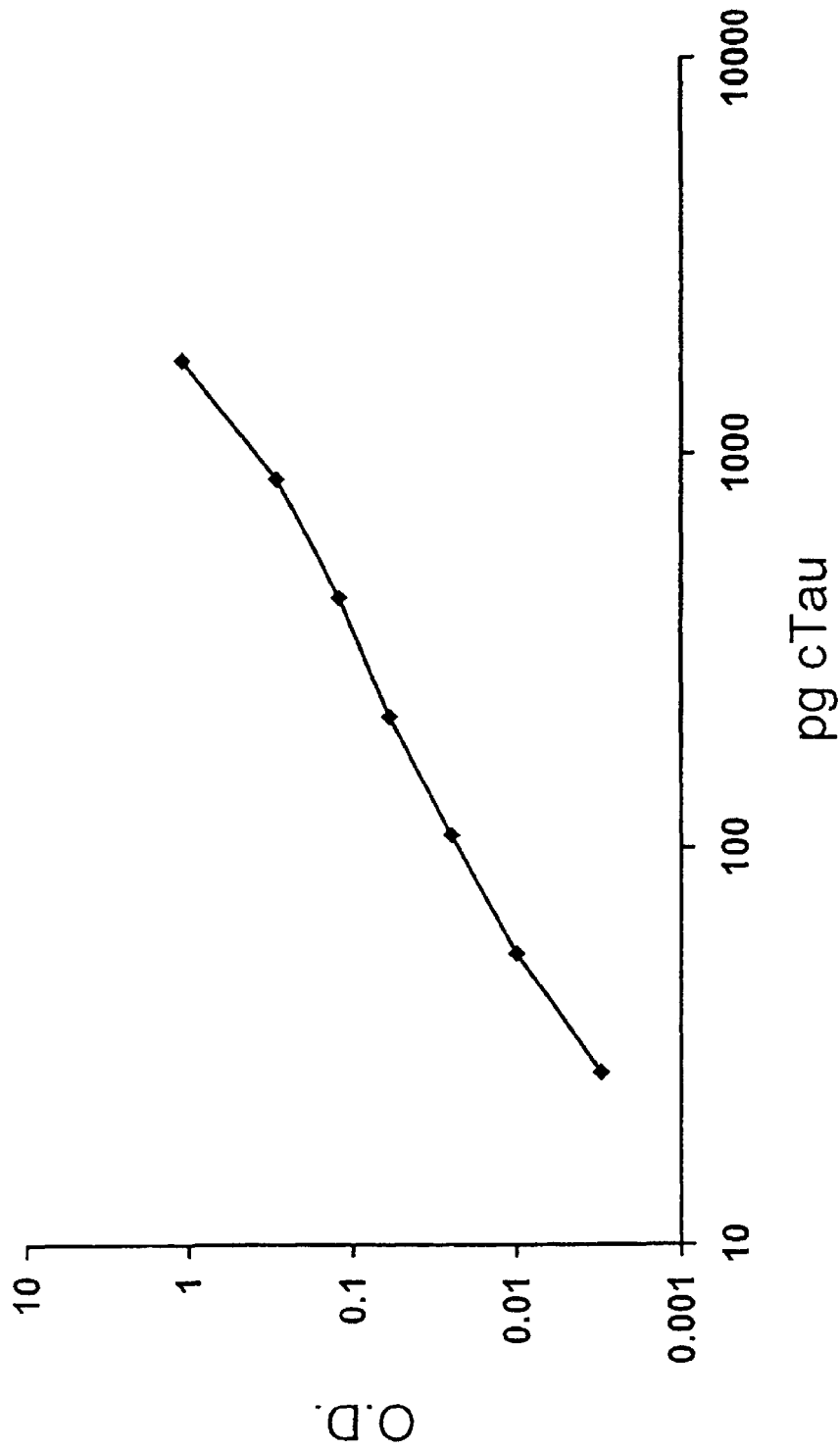

Fig. 6. Titration of affinity purified CSF cleaved tau employing the developed cleaved tau ELISA. A catalyzed-reporter deposition sandwich ELISA was developed employing cTau12 as capnure antibody and HRP-conjugated cTau7 and cTau8 for decetion. Affinity purified CSF cleaved tau was used as standard. All concentrations (pg/well) were tested in triplicate and values represent the mean O.D. value.

METHOD OF DETECTING AXONAL DAMAGE, FROM ASSOCIATED DISEASE STATES USING TAU MONOCLONAL ANTIBODIES

FIELD OF THE INVENTION

The present invention is in the field of clinical and diagnostic testing, and relates generally to a method of detecting axonal damage and associated disease states.

BACKGROUND OF THE INVENTION

Axonal degeneration is a primary feature of brain injury in humans (Hayes et al., 1995). The present invention describes several methods of assessing axon degeneration in humans by measuring proteins that are localized in axons. These axonal proteins are released following head injury into the extracellular space and are transported to cerebrospinal fluid (CSF). Methods are disclosed in the present invention for measuring these axonal proteins in the CSF of patients.

Tau protein is a major microtubule associated structural protein localized primarily in axons (Binder et al. 1985; Kosik and Finch 1987). The localization of tau in axons is thought to result from the preferential sequestration of tau mRNA in the proximal portion of axons (Litman et al., 1993) and the selective stabilization of tau in axons (Kanai and Hirakawa 1995). Human tau proteins are encoded by a single gene and at least six alternately spliced isoforms have been identified that demonstrate an apparent molecular weight of 48 kilodalton (kDa) to 68 kDa (Goedert et al. 1989 and FIG. 5; See e.g., SEQ ID No. 1) Under normal conditions, little or no tau is released extracellularly. This disclosure teaches that tau is released under clinical conditions associated with axon damage.

Neurofilament proteins, similar to tau, are structural neuronal proteins found in central nervous system axons (Shaw, 1986). Neurofilaments that are the subject of the present invention consist of four separate protein elements: 1) a light neurofilament subunit (neurofilament-L) with an apparent molecular weight of 68 kDa, 2) a medium-sized neurofilament subunit (neurofilament-M) with an apparent molecular weight of 160 kDa, 3) a heavy neurofilament subunit (neurofilament-H) with an apparent molecular weight of 200 kDa, and 4) neurofilament66/α-internexin (neurofilament66) with an apparent molecular weight of 66 kDa (Lee and Cleveland, 1996). These neurofilaments are each encoded on a separate gene (Julien et al., 1987; Myers et al., 1987; Lees et al., 1988; Chan and Chiu, 1995). Following head injury neurofilaments are depleted from degenerating axons and gain access to the CSF (Hayes et al., 1995).

One clinical condition associated with axonal degeneration is head trauma. Axonal injury, clinically referred to as diffuse axorial injury, accounts for about half of the primary lesions observed in closed head trauma and is one of the most frequent causes of poor clinical outcome. MRI is the procedure of choice for detecting diffuse axonal injury, however, MRI routinely underestimates the true extent of the damage. One embodiment of the present invention involves the development and use of an alternative procedure for quantifying axon damage in patients with CNS injury.

Another embodiment of the present invention involves a method for quantifying axonal degeneration which is the central feature of neurodegenerative disorders including Alzheimer's disease. Alzheimer's disease is a progressive, degenerative disease that attacks the brain and results in impaired memory, thinking and behavior. Alzheimer's disease is the most common form of dementia, which is the loss of intellectual function so severe it interferes with daily life. Since being first described by Dr. Alois Alzheimer in 1906, it has become the fourth leading cause of death among adults in the United States between the ages of 75 and 84. The clinical mortality and morbidity seen in Alzheimer's patients directly results from neuronal death in the brain. In neurodegenerative disorders including Alzheimer's disease, neuronal death is always accompanied by axonal degeneration.

To determine the existence vel non of disease or trauma states associated with axonal damage in a patient, it is desirable to be able to ascertain whether a patient has such axonal damage and to quantify such damage.

Accordingly, it is desirable to be able to perform convenient and reliable tests for tau proteins or neurofilament proteins in order to test for axonal damage. It is also desirable to have available such tests that may be used on ante mortem or post mortem patient samples.

In view of the present disclosure or through practice of the present invention, other advantages or problem solutions may become apparent.

SUMMARY OF THE INVENTION

The present invention includes a method of determining the extent of axonal damage in the human CNS, novel cleaved forms of tau proteins and neurofilament proteins associated with axonal damage, and monoclonal antibodies (Mabs) raised against novel cleaved forms of tau protein useful in such a method.

In general terms, the method of the present invention is a method of determining axonal damage in the human CNS, the method comprising the steps: (a) obtaining a sample of CSF from the human central nervous system of a patient; (b) treating the sample of CSF with monoclonal antibody(ies) binding to novel cleaved form(s) of tau proteins or neurofilament proteins described in the present application; and (c) detecting the presence and/or level of the cleaved form(s) of the tau proteins or neurofilament proteins bound to the monoclonal antibody(ies).

The method of the present invention may also include the step of comparing the amount of the cleaved form(s) of the tau proteins or neurofilament proteins bound to the monoclonal antibody(ies) in step (c) to control samples selected from the group consisting of those representing a normal undamaged axon state and those representing an axonal damage state.

The method of the present invention may be used to detect cleaved form(s) of tau proteins or neurofilament proteins. The cleaved tau protein(s) of particular interest in the present method are those having an apparent molecular weight less than 50 kDa and being in a phosphorylated or non-phosphorylated state, particularly those fragments in the range of about 30 kDa to 50 kDa. The present method also has been forced to characterize the multiple protein bands comprising these 30 kDa to 50 kDa tau protein fragments. The cleaved neurofilament proteins of particular interest in the present method occur in human CSF where they demonstrate an apparent molecular weight: 1) for neurofilament-L less than is 68 kDa, 2) for neurofilament-M less than 160 kDa, 3) for neurofilament-H less than 200 kDa, and for neurofilament66 less than 66 kDa.

The method of the present invention may be used to determine whether axonal damage has occurred and to what extent, and thus can be used to determine the existence or likelihood of any disease state associated with axonal damage, such as CNS injuries, including primary neuronal injuries (e.g., cortical contusion, diffuse axonal injury, subcortical gray matter injury and primary brain stem injury), primary hemorrhages (e.g., subdural hematoma, epidural hematomas, intracerebral hematoma and diffuse hemorrhages), primary vascular injuries (e.g., arterial psuedoaneurysm, arterial dissection/occlusion), dural sinus laceration/occlusion, traumatic pia-arachnoid injuries, cranial nerve injuries and secondary traumatic lesions (e.g., infarction, hypoxic injury, diffuse brain swelling/edema, secondary hemorrhage), central nervous system tumor, neurodegenerative diseases of the central nervous system including Alzheimer's disease, spinal cord injury, acute cerebral vascular accident or axonal damage following ingestion of drug(s) or poison(s).

The present invention also includes cleaved forms of tau proteins having an apparent molecular weight less than 50 kDa particularly those fragments in the range of about 30 kDa to 50 kDa, and being in a substantially isolated and/or purified form. The present invention also includes cleaved forms of neurofilament proteins in a substantially isolated form occuring in human CSF where they demonstrate an apparent molecular weight: 1) for neurofilament-L less than 68 kDa, 2) for neurofilament-M less than 160 kDa, 3) for neurofilament-H less than 200 kDa, and for neurofilament66 less than 66 kDa. These substances may be used as standards or controls in tests using the present invention.

Substantially isolated and/or purified Mabs raised against at least one tau protein and/or its cleaved forms, and having been screened against human CSF are also included in the present invention. As used herein, a substantially isolated or substantially purified monoclonal antibody consists of a single hybridoma clone recognizing a single protein epitope essentially free of contaminating or interfering molecules. It is preferred that such Mabs are those raised against tau protein fragments, and having been screened against human CSF, said monoclonal antibody being in a substantially isolated form, and said tau protein fragment comprising the peptide sequence including the amino acids from serine$^{199}$ to serine$^{396}$ of tau protein, and lacking the native N-terminal and C-terminal amino acids. These substances are useful in the methods of the present invention.

The present invention can also be used to ascertain or predict the severity of neurologic trauma, such as intercranial lesions, or the neurologic disease states giving rise to tau or neurofilament proteins in CSF, such as those disease states discussed above and/or to ascertain or predict clinical outcome following such trauma.

DESCRIPTION OF FIGURES

FIG. 1. Monoclonal antibodies recognizing cerebrospinal fluid cleaved tau proteins were developed by differential CSF screening.!24 Left panel: Initial studies demonstrated that Mab Tau-1 labeled 30 kD to 50 kD CSF proteins in CNS trauma patients (TRA; lane a 50 μl CSF, lane b 10 μl CSF) but not normal controls (CNT; lane c and d both 50 μl CSF). Right panel: Mabs were developed that specifically recognized 30 kD to 50 kD CSF tau proteins employing a differential CSF screen. Hybridomas were selected that labeled CSF from CNS trauma patients (lanes a–d) but not control patients (lanes e–h). The same patient samples were run in lanes a and b in left and right panels. cTau7 lanes a and e–h 50 μl CSF, lanes b–d 10 μl CSF. Molecular weight markers shown at right.

FIG. 2. CSF cleaved tau Mabs label recombinant tau. Commassie Blue stained 10% gel with recombinant 3-repeat tau (Gel, left lane, !1 μg) and 4-repeat tau (Gel, right lane, 1 μg). Recombinant tau blotted with BYA (0.07 μg/lane) and cTau12 (2.5 μg/lane). Molecular weight markers shown at right.

FIG. 3. CSF cleaved tau proteins bind microtubules. Microtubule Purified: Initially, taxol polymerized microtubules were salt extracted to insure that no cTau7 immunoreactive proteins were present (lane a). Microtubules were then incubated with a preparation of CSF cleaved tau proteins (lane b, 1 μg) and washed several times until the supernatant was free of cTau7 reactivity (lanes c and d). Microtubule bound proteins were salt extracted yielding 30 kD to 50 kD cTau7-reactive cleaved tau proteins (lane e). Similar results were obtained with Mabs cTau8 and cTau12 (data not shown). Affinity Purified: CSF cleaved tau proteins were affinity purified with Mabs cTau7, cTau8 and cTau12 coupled to Protein G agarose. Commassie Blue stained gels indicated that affinity purified cleaved tau consisted of a primary 50 kD protein band (gel, 1 μg). Immununoblots with cTau7 revealed a single protein band when 10 nanograms (ng) of affinity purified cleaved tau protein was loaded; lower molecular weight cTau7 reactive proteins were detected with larger protein loads (30 and 100 ng). Similar results were observed with Mabs cTau8 and cTau12 (data not shown).

FIG. 4. Mabs cTau7, cTau8 and cTau12 recognize a 14.7 kDa CNBr cleaved tau digestion fragment occurring in patient CSF or Brain. Cleaved tau from CSF or brain (2 μg/lane) was treated either with (+) or without (0) CNBr and blotted with Mabs PHF-1, cTau7, cTau8 and cTau12. All four antibodies predominantly labeled the same CNBr digestion fragment in both CSF and brain consisting of pro$^{251}$ to met$^{419}$ of tau. The PHF-1 fragment has a reported molecular weight of 14.7 kDa (Zemlan and Dean, 1996). Blots are from a 15% gel. The position at which non-digested cleaved tau migrated is shown (Tau).

FIG. 5. CNS trauma brain contains both full length 48 kD to 68 kD tau proteins and 30 kD to 50 kD cleaved tau proteins. Full length brain tau proteins were selectively labeled with the tau antibody BYA, the C-terminal tau antibody Alz5 and the N-terminal tau antibody Alz50. Cleaved tau proteins were selectively labeled with Mabs cTau7, cTau8, cTau12 and PHF1 that recognizes phosphoser$^{396}$ of tau. Mab Tau-1 that recognizes non-phosphorylated ser$^{199}$ of tau labeled both forms of tau. These data suggest that tau is cleaved and phosphorylated at ser$^{199}$ in brain.

FIG. 6. Titration of affinity purified CSF cleaved tau employing the developed cleaved tau ELISA. A catalyzed-reporter deposition sandwich ELISA was developed employing cTau12 as capture antibody and HRP-conjugated cTau7 and cTau8 for detection. Affinity purified CSF cleaved tau was used as standard. All concentrations (pg/well) were tested in triplicate and values represent the mean O.D. value.

DETAILED DESCRIPTION OF INVENTION

The proteins that are useful in the present invention are a novel class of axonally-derived proteins occurring in human CSF including cleaved tau proteins and cleaved neurofilament proteins. As used herein, axonally-derived proteins refer to a group of proteins that occur in axons of CNS neurons and are released into the extracellular space during degeneration of said axons. As used herein, the term full length tau refers to any of the six non-cleaved isoforms of this protein that demonstrate an apparent molecular weight of 48 to 68 kDa and whose genomic and amino acid sequences are described in Goedert et al. (1989). The class of novel cleaved tau proteins that are useful in the invention were discovered in human cerebrospinal fluid and have been purified. These novel cleaved tau proteins may be distinguished from previously described full length tau proteins, in that they: 1) have reduced apparent molecular weights in comparison to full length tau, 2) are comprised of the interior portion of the tau sequence that includes ser$^{199}$ to ser$^{396}$ of tau, and 3) lack the N-terminal and C-terminal amino acids of tau. As used herein, the term neurofilament-L refers to a protein with an apparent molecular weight of 68 kDa and whose genomic and amino acid sequences are described in Julien et al. (1987). As used herein, the term neurofilament-M refers to a protein with an apparent molecular weight of 160 kDa and whose genomic and amino acid sequences are described in Myers et al. (1987). As used herein, the term neurofilament-H refers to a protein with an apparent molecular weight of 200 kDa and whose genomic and amino acid sequences are described in Lees et al. (1988). As used herein, the term neurofilament66 refers to a protein with an apparent molecular weight of 66 kDa and whose genomic and amino acid sequences are described in Chan and Chiu (1995).

Antibodies specifically reactive with the novel cleaved tau proteins are included within the scope of the invention. A "specifically reactive" antibody is one that is capable of binding with a particular molecule to thereby couple said molecule to the antibody. The term "epitope" refers to that portion of a hapten which can be recognized and bound by an antibody. The present disclosure indicates that the antigen employed for monoclonal antibody production, a cleaved form of tau found in human cerebrospinal fluid, possesses more than one epitope. An antigen is a molecule capable of inducing an animal to produce an antibody capable of binding to an epitope of that antigen. The specific reaction referred to above is meant to indicate that an antibody will bind with a significantly higher affinity to its corresponding antigen as opposed to the multitude of other antigens occurring in the human body. For example, there is provided by this invention several Mabs (i.e. cTau-7, cTau-8 and cTau-12) raised against the cleaved form of tau found in CSF. These cTau antibodies demonstrated sufficiently higher affinity for cleaved tau than for full length tau such that selective immunolabeling of cleaved tau occurred with equivalent protein loads on Western blots.

EXAMPLE

Purification, Characterization and Measurement of Human Cerebrospinal Fluid Cleaved Tau Proteins in Patients with Axonal Degeneration

Summary of Example

Tau proteins are structural axonal proteins associated with microtubule stabilization. Under normal conditions tau is a non-released intraneuronal protein, however, the disclosure teaches that tau gains access to the CSF during axon degeneration. As described in the present disclosure, the cleaved form of tau proteins found in human CSF during axon degeneration were purified, characterized and Mabs that selectively bind to this novel cleaved form of tau developed. These monoclonals were employed to develop a sandwich ELISA for measuring CSF cleaved tau. Employing this ELISA, patients with axonal degeneration demonstrated CSF cleaved tau levels 10,000 times higher than patients without axonal degeneration; no overlap in CSF cleaved tau levels between the two groups of patients was observed.

Materials and Methods

CSF Samples

CSF samples were collected under an approved protocol from the University of Cincinnati Institutional Review Board. CSF was collected from hospitalized patients with severe brain injury (Glasgow Coma Scale <10) resulting from trauma or intracranial aneurysmal rupture via intraventricular catheters. CSF was collected by lumbar puncture from control patients. CSF samples were centrifuged at 13,000 g for 15 min and stored at $-70°$ C. until use.

Protein Purification and Expression

Tau purification, dephosphorylation and digestion. Tau was purified using a procedure modified from Nukina et al. (1987). Briefly, post mortem human brains were homogenized in a volume 2.5 times the weight in 50 mM Tris-HCl (pH 6.8), 0.3 M NaCl, 1% β-mercaptoethanol (BME), 1 mM PMSF and 5 μM leupeptin. The homogenate was centrifuged at 30,000×g for 5 min at 4° C. The supernatant was incubated on ice and the pellet homogenized a second time in a volume 2.5 times the weight with 50 mM Tris-HCl (pH 9.2), 0.3 M NaCl, 1% BME. The homogenate was then centrifuged at 4° C. for 5 min at 30,000×g. The supernatants were combined and boiled for 10 min. The samples were then spun for 30 minutes at 30,000×g at 4° C. The samples were dialyzed overnight against 50 mM Tris-HCl before examination by SDS-PAGE. Tau antigen was prepared by running the tau preparation on 10% SDS-polyacrylamide curtain gels. Proteins with molecular weights of 30 kDa to 80 kDa were excised and electroeluted in a Schleicher & Schuell (Keene, N.H.) Elutrap device containing 40 mM Tris-borate buffer (pH 8.64) and 0.8% SDS, then dialyzed against 50 mM Tris-HCl prior to injection. Brain and CSF tau proteins were dephosphorylated overnight at 37° C. in 50 mM Tris-HCl (pH 8.0) with or without 1 U/ml bacterial alkaline phosphatase (BAP; Sigma Chemical Co.). The effect of BAP treatment on Mab binding was assessed by solid phase ELISA. Wells were coated with 300 ng of tau, blocked and washed, and primary antibody added for 1 hr and assayed as described below. For epitope mapping studies, tau samples were digested in 200 μl of 70% formic acid containing 50 mg/ml cyanogen bromide (CNBr) solution and incubated overnight at room temperature. Samples were washed twice with 1 ml ddH$_2$O and evaluated on 15% SDS-PAGE gels.

Purification of microtubules. Tubulin was purified from rat brain and microtubules assembled in the presence of taxol (Schiff et al., 1979; Vallee, 1982). Microtubule-associated proteins (MAPs) were dissociated from the microtubules by suspending the microtubule pellet (600 μg) in assembly buffer (40 μM taxol in 0.1 M PIPES, 1.0 mM EGTA, 1.0 M MgSO$_4$ and 1.0 mM GTP,) and NaCl added to a final concentration of 0.35 M. CSF and brain samples were incubated with shaking for 10 min at 37° C. and centrifuged at 30,000×g for 25 min. After repeated salt extractions (3×), all MAPs had been removed from the microtubule samples as judged by Western blots of the third supernatant probed with BYA.

MAP purification. NaCl was removed from the above microtubule pellet (600 μg) by washing in 1.3 ml of assembly buffer. Microtubules were pelleted at 30,000×g for 25 min; CSF or human heat-stable proteins containing tau and 1.3 ml assembly buffer were added to the pellet, incubated for 10 min at 37° C., and centrifuged at 30,000×g for 25 min. Proteins not bound to microtubules were removed by two cycles of washing (1.3 ml assembly buffer, incubation for 10 min at 37° C., centrifugation at 30,000×g for 25 min). Microtubule bound proteins were dissociated by the addition of 0.5 ml of assembly buffer with 0.35 M NaCl to the washed microtubule pellet. Following incubation for 10 min at 37° C. the sample was dialyzed against 50 mM Tris-HCl and analyzed by immunoblotting.

Recombinant tau. Recombinant human tau was produced using the previously described pET-n123c and pET-n1234c plasmids expressed in the BL21(DE3) expression vector (Lee and Rook, 1992). The plasmids were the generous gift of Dr. Gloria Lee. Plasmid pET-n123c codes for the 352 amino acid three repeat form of tau while plasmid pET-n1234c codes for the 383 amino acid four repeat form of tau containing exon 10. Following expression tau was purified as above and was estimated to be approximately 90% pure as judged by Commassie Blue stained SDS-PAGE.

Monoclonal Antibody Production

Monoclonal human cleaved tau antibodies. Female Balb/C mice were injected interperitoneally with 100 g of the antigen preparation suspended in an equal volume of Freund's complete adjuvant (Sigma, St. Louis, Mo.). Boosts were performed at two week intervals with 100 µg of the antigen suspended in incomplete Freund's adjuvant (Sigma). Mice were bled prior to each boost and sera titered by ELISA. Mabs were produced as previously described (Kohler and Milstein, 1975). Briefly, $1.8 \times 10^8$ spleen cells were mixed with $3.6 \times 10^7$ NS1/1-Ag4 mouse myeloma cells. Fusion was induced by addition of 38% polyethylene glycol 1550. Cells were washed with DMEM (Gibco BRL, Gaithersburg, Md.) and resuspended in Super DMEM (Gibco BRL) containing 14% fetal calf serum and HAT (Sigma). Cells were dispersed in 96-well microtiter plates coated with a mouse splenocyte feeder layer. Supernatants were screened after plating against CSF from CNS trauma patients or controls by ELISA and Western blot. Colonies that produced supernatant found to react with CSF from CNS trauma patients but not control CSF were expanded and cloned by limiting dilution. To insure isolation of monoclonal hybridomas, cloning was repeated until 100% of the wells showed specific Mab production. At the end of this process, three Mabs, designated cTau7, cTau8 and cTau12 were recovered.

Ascites production. Male Balb/C mice were primed by IP injection of 0.5 ml pristane (Sigma) followed 14 days later by injection of $10^6$ hybridoma cells. After seven days, the peritoneal cavities were tapped. Ascites fluids were titered, pooled by hybridoma and stored at −20° C. To ensure establishment of stable cell lines, hybridomas were passed twice through pristane primed mice. Following each passage, hybridomas were recloned. Stability was defined as 100% of hybridoma supernatants exhibiting immunoreactivity against antigen by ELISA. Stable hybridomas were then injected into mice and ascites collected for Mab purification (below).

Mab purification and tau affinity purification. One ml of ascites was diluted 1:1 with 50 mM sodium acetate (pH 5.0) and applied to 2 ml of equilibrated Protein G sepharose. After washing, Mabs were eluted with Gentle Ag/Ab Elution Buffer (Pierce, Rockford, Ill.) and desalted over sepharose G-25 (2SQ-B, Isolab, Inc., Akron, Ohio). Mab purity was confirmed by isoelectric focusing using Resolve™ agarose IEF gels (Isolab, Akron, Ohio) and SDS-PAGE. Purified Mabs 7A5, 8A12 and 12B2 were used to affinity purify human tau using Protein G-agarose (Boehringer Mannheim, Germany) as specified by the manufacturer. Purified Mabs were conjugated to horseradish peroxidase (HRP; Finnsugar) as described in Boorsma and Kalsbeek (1975). A checkerboard titration was performed to determine the optimal conjugate dilution for ELISA and immunoblot studies.

Antibodies

Mabs PHF-1 (IgG, 1:500) and Alz50(IgM, 1:10) both raised against a PHF preparation (Wolozin et al., 1986; Greenberg et al., 1992) were the generous gift of Dr. Peter Davies. Mab SMI33 (IgM, 1:750) that recognizes non-phosphorylated $ser^{235}$ of tau (Lichtenberg-Kraag et al., 1992) was purchased from Sternberger Monoclonals Inc (Baltimore, Md.). Polyclonal antibody BYA-1074 (1:1,000) raised against bovine tau (Kosik et al., 1989) and tau Mab Tau-1 (IgG, 1:500) that recognizes non-phosphorylated $ser^{199}$ of tau (Liu et al., 1993) were purchased from Accurate Chemical & Scientific Corp. (Westbury, N.Y.). Polyclonal antibody Alz5 (1:300) was raised against a synthetic peptide corresponding to the C-terminal 13 amino acids of tau (Caputo et al., 1992).

Immunoblotting

CSF or non-digested brain proteins were run on 10% SDS-polyacrylamide gels (Laemmli, 1970) and transferred electrophoretically to nitrocellulose (BA-S 85, Schleicher & Schuell, Keene, N.H.) as described by Towbin (1979). Nonspecific binding was blocked with 5% BSA in TBST (0.1 M Tris-HCl, 0.9% NaCl, with 0.1% (v/v) Tween 20) for 1 hr. The membrane was washed for 30 minutes in TBST, incubated with primary antibody for 1 hr, and blocked in 5% nonfat dry milk in TBST for 15 minutes. After washing (3 times in TBST), a 1:200 dilution of biotinylated secondary antibody (Vector Laboratories, Burlingame, Calif.) in TBST was added for 30 minutes, the membrane washed and then transferred to Vectastain ABC-peroxidase (Vector Laboratories) in TBST for 30 minutes. The blot was washed and transferred to a substrate solution of diaminobenzidine tetrahydrochloride dehydrate in phosphate-buffered saline (PBS) with 1% $NiCl_2$ and 1% $CoCl_2$. Mabs cTau7, cTau8 and cTau12 were diluted 1:1,000 for immunoblots.

Enzyme-Linked Immunosorbent Assay

Tau sandwich ELISA. Immulon 2 plates were coated with affinity purified Mab cTau12 (100 µl/well, 5 µg/ml) for 1 h and overcoated overnight with 5% nonfat dry milk and 0.5% gelatin in TBS. Plates were washed with TBST, 100 µl/well of affinity purified tau was added (27 pg to 1,720 pg), the plates incubated for 1 h and then washed with TBST. A 1:1 mixture of HRP-conjugated Mabs cTau7 and cTau8 (100 µl/well, 1:2,000) was added, and the plates incubated for 1 h and washed with TBST. Biotin-tyramine (100 µl, 3 µg/ml in 50 mM Tris-HCl, 0.001% $H_2O_2$, pH 8.0) was added for 15 min and plates washed (Bobrow et al, 1989). Color was developed with Vector ABC-AP using nitrophenylphosphate as substrate and read at 405 nm. Negative controls included exclusion of cTau12, deletion of tau, or cTau7 and cTau12 from the assay.

Results

CSF Cleaved Tau Monoclonal Antibodies

CSF from CNS injury and control patients was immunoblotted with Mab Tau-1 whose epitope has been mapped to $ser^{199}$ of tau. Distinct but modest Tau-1 labeling of CSF proteins in the 30 kDa to 50 kDa region was observed in CNS injury patients while no immunoreactivity occurred in control patients (FIG. 1). Mabs recognizing these 30 kDa to 50 kDa CSF cleaved tau proteins were developed by subjecting hybridoma supernatants to a differential solid phase ELISA screen employing CSF samples from CNS injury and control patients. Three monoclonal producing hybridomas, cTau7, cTau8 and cTau12 were selected that maximally discriminated between CNS injury and control CSF (FIG. 1). For example, cTau7 CSF immunoblot data from four CNS trauma patients are shown in FIG. 1. CSF samples in the first and third lanes were from two different closed head injury patients with intracranial hemorrhage while CSF samples in the second and fourth lanes were from two different patients with subarachnoid hemorrhage secondary to rupture of the anterior communicating artery. All patients were admitted with a Glasgow Coma Score less than 7 and demonstrated elevated intracranial pressure requiring placement of an intraventricular shunt. All four CNS trauma patients demonstrated significant cTau7 labeled CSF proteins in the 30 kDa to 50 kDa range. In comparison, control patients demonstrated no cTau7 immunoreactivity (FIG. 1). Similar results were observed with CSF samples immunoblotted with cTau10 and cTau12 (data not shown). The developed Mabs resulted in more intense labeling of CNS trauma patient CSF than Tau-1. Split CSF samples with equivalent protein loads were blotted with Tau-1 (FIG. 1, left panel, lanes a and b) and cTau7 (FIG. 1, right panel, CNS trauma, lanes a and b) with cTau7 producing more intense labeling.

Characterization of cTau7, cTau8 and cTau12 Labeled Proteins

The experiments described below indicate that the 30 kDa to 50 kDa proteins recognized by antibodies cTau7, cTau8 and cTau12 are a cleaved form of the microtubule binding protein tau. These data demonstrate that: 1) antibodies cTau7, cTau8 and cTau12 label recombinantly expressed tau, 2) that the 30 kDa to 50 kDa proteins recognized by cTau7, cTau8 and cTau12, similar to tau, contain a functionally intact microtubule binding domain, 3) antibodies cTau7, cTau8 and cTau12 label a 14.7 kDa CNBr digestion fragment comprised of pro$^{215}$ to met$^{419}$ of the tau primary sequence, 4) 30 kDa to 50 kDa cleaved tau proteins occur in both CSF from CNS trauma patients and post mortem brain and 5) epitope mapping studies suggest that CSF 30 kD to 50 kD proteins consist of the interior portion of the tau sequence from which the N- and C-terminal amino acids have been cleaved.

Recombinant tau immunoreactivity. Mabs cTau7, cTau8 and cTau12 labeled recombinant tau expressed in *E. coli* (FIG. 2). Recombinant tau containing either three repeats or four repeats was expressed in BL21(DE3) cells and isolated. Recombinant tau was highly purified as judged by Commassie Blue stained SDS-PAGE (FIG. 2, Gel). Both tau isoforms demonstrated immunoreactivity with tau polyclonal antibody BYA and at higher protein loads Mabs cTau12 (FIG. 2), cTau7 and cTau8 (data not shown).

Affinity and microtubule purification of tau. CSF from CNS trauma patients or a preparation of heat-stable brain proteins was affinity purified with Mabs cTau7, -8 and -12 (FIG. 3). Affinity purification from either source revealed a band of 30 kDa to 50 kDa tau proteins on immunoblotting or on Commassie Blue stained SDS-PAGE (FIG. 3, Affinity Purified). These data suggest that 30 kDa to 50 kDa tau proteins are cleaved in brain and then gain access to CSF.

Similar to tau, CSF and brain 30 kDa to 50 kDa proteins recognized by Mabs cTau7, cTau8 and cTau12 bind microtubules. Tubulin was purified from brain and polymerized into mictotubules with taxol. Endogenous microtubule binding proteins were dissociated from the polymerized microtubules with all detectable endogenous MAPs removed by the third salt extraction (FIG. 3, lane a). Microtubules were incubated with CSF 30 kDa to 50 kDa cleaved-tau proteins (FIG. 3, lane b) and microtubules washed several times to remove all proteins not tightly bound (FIG. 3, lanes c and d). Microtubule binding proteins were then salt extracted from the washed microtubule preparation revealing a cTau7-labeled ladder of 30 kDa to 50 kDa proteins (FIG. 5, lane e). Similar results were obtained with Mabs cTau8 and cTau12 (data not shown). No labeling of MAP2 or neurofilaments with Mabs cTau7, 8 and 9 was observed in the microtubule purified brain preparation. The presence of 280 kDa MAP2 in this preparation was confirmed by immunoblots with Mab AP-14 (Kalcheva et al., 1994) which labels both MAP2a and MAP2b while the presence of 200 kDa neurofilament-H and 155 kDa neurofilament-M was confirmed with Mabs NE-14 (Gotow and Tanaka, 1994) and BF-10 (Anderton et al., 1982), respectively (data not show).

Epitope mapping. cTau7, -8 and -12 immunoblots of CNBr digested CSF or brain 30 kDa to 50 kDa tau proteins indicated that all three Mabs labeled the same CNBr fragment (FIG. 4). This fragment could also be labeled with the Mab PHF-1 which recognizes phosphorylated ser$^{396}$ of tau (Otvos et al, 1994; Zemlan et al., 1996). The PHF-1 data identify the cTau7, cTau8 and cTau12 labeled fragment as the largest CNBr digestion product that is comprised of tau sequences pro$^{251}$ to met$^{419}$. These data indicate that both CSF and brain cleaved tau proteins demonstrate similar CNBr digestion products suggesting that the labeled CSF and brain proteins are structurally similar.

Tau antibody BYA raised against full length tau labeled a band of 48 kDa to 68 kDa proteins in heat-stable extracts of post mortem brain (FIG. 5). In comparison, antibodies cTau7, -8 and -12 labeled a band of 30 kDa to 50 kDa proteins indicating that these cTau Mabs labeled proteins demonstrating an greater gel mobility than intact tau. Further, these data indicate that Mabs cTau7, cTau8 and cTau12 have limited affinity for intact, full length tau. Mab PHF-1 also selectively labeled a band of 30 kDa to 50 kDa proteins indicating that these proteins differ from intact tau both by cleavage and phosphorylation at ser$^{396}$ (FIG. 5, PHF1). Mab Tau-1 labeled proteins spanning the 30 kDa to 68 kDa region indicating that ser$^{199}$ is poorly phosphorylated in both full length and cleaved tau (FIG. 5, Tau1). In comparison, the C-terminal antibody Alz5 and the N-terminal antibody Alz50 labeled only full length tau suggesting that these epitopes are not present in cleaved tau.

To determine whether tau cleavage occurred in CSF, 5 μg of recombinant tau was added to 1 ml of CSF and incubated overnight at 37° C. CSF aliquots were run on SDS-PAGE and blotted with BYA which indicted the presence of intact, noncleaved tau in all cases.

Prior to sandwich ELISA development, it was important to determine whether cTau7, cTau 8 and cTau12 epitopes were independent and whether the epitopes were phosphorylated. ELISA competition studies between cTau7, cTau8 and cTau12 resulted in non-competitive binding to CSF tau proteins (data not shown). Also, Mabs cTau7, cTau8 and cTau12 demonstrated phosphorylation independent binding to 30 kDa to 50 kDa cleaved tau proteins. For example, BAP treatment produced a 5 fold increase in the binding of Mab SMI33 which recognizes non-phosphorylated ser$^{235}$ of tau (BAP: 1.88, no BAP: 0.35, mean O.D.) while no effect of BAP treatment on cTau7 (BAP: 1.75, no BAP 1.51), cTau8 (BAP: 1.99, no BAP: 1.61) or cTau12 (BAP: 1.72, no BAP: 1.53) binding was observed.

Cleaved Tau Sandwich ELISA and Axonal Degeneration

A sensitive ELISA using catalyzed reporter deposition for signal enhancement was developed using Mab cTau12 for antigen capture, HRP-conjugated Mabs cTau7 and cTau8 for detection, and biotin-tyramine as the reporter. The sensitivity of this ELISA for affinity purified CSF tau was about 0.030 ng to 0.040 ng per well (FIG. 6).

This ELISA was employed to measure CSF cleaved tau levels in patients undergoing active axonal degeneration. CSF was obtained from 131 patients. Samples were collected from patients with axonal degeneration resulting from acute CNS injury and three control groups free of axonal degeneration (demyelinating disease, neurologic controls and normal controls). The CNS injury group consisted of patients with acute severe brain injury resulting from trauma or intracranial aneurysmal rupture. The demyelinating disease group consisted exclusively of patients with multiple sclerosis (N=41). The neurologic control group consisted of patients with migraine or vascular headache (N=9), dementia not associated with a neurodegenerative disease (N=11), myotonic disorder (N=4), seizure disorder (N=3), Guillian-Barre syndrome (N=2), hydrocephalus (N=2), seizure disorder (N=2), transverse myelitis (N=2) or other neurologic disorder (N=3). The normal control group were individuals with no known neurologic disease. They consisted of family members of patients with a neurologic disease (N=10), patients with a psychiatric disorder (N=13) or patients hospitalized for a non-neurologic disorder (N=18).

CSF cleaved tau levels were significantly elevated in patients with axonal degeneration following CNS injury (Table 1). CSF cleaved tau levels were elevated over 10,000 fold in CNS injury patients when compared to patients without axonal degeneration, i.e. a demyelinating disease ($p<0.001$), or neurologic controls ($p<0.001$) or normal controls ($p<0.001$). Further, no overlap between CNS injury CSF cleaved tau levels and patients in any control group were observed. Only two of the 41 patients in the demyelinating disease group demonstrated detectable tau levels and both values were significantly lower than those observed in the CNS injury group. Similarly, CSF cleaved tau levels were not detectable in most control patients. Among neurologic controls only two of 38 patients had detectable CSF tau levels. These were patients with Guillian Barre syndrome (0.464 ng/ml) or cerebral ischemia (0.433 ng/ml). Only one of 41 normal control patients demonstrated detectable tau levels. This was a cardiac transplant patient (0.927 ng/ml).

Conclusion

In the present disclosure, a novel cleaved form of tau is described in CSF. This truncated form of tau was reactive with the three Mabs developed in the present study and tau antibodies raised in other laboratories (FIGS. 1 and 5). The present data indicate that only cleaved tau and not full length 48 kDa to 68 kDa tau proteins are present in CSF (Cleveland et al., 1977; Couchie and Nunez, 1985). Consistent with these data, differential CSF hybridoma screening identified three Mabs that demonstrated high affinity for the cleaved form of tau found in CSF but limited affinity for intact, full length tau (FIG. 5). For example, Mabs cTau7, cTau8 and cTau12 demonstrated selective labeling of cleaved tau when equivalent protein loads of cleaved tau and intact were examined by Western blot (FIG. 5). Similarly, thirty fold greater protein loads of full length recombinant tau were required to demonstrate labeling with cTau7, cTau8 and cTau12 than with antibodies raised against full length tau (FIG. 2).

The selectivity of Mabs cTau7, cTau8 and cTau12 for cleaved tau is best explained by a conformational state assumed by tau following cleavage rather than differences in primary sequence or phosphorylation. Previous research demonstrates that Mabs can specifically recognize tau secondary structure. Several tau Mabs including Alz50, Tau-2 and MC1 recognize a specific tau conformation rather than tau primary structure (Carmel et al., 1996; Vincent et al., 1996). For example, using tau deletion mutants Carmel et al. (1996) demonstrated that Alz50 recognized a conformation of tau where the N-terminus is in close association with the microtubule binding domain. The $K_d$ of Alz50 for the native tau protein in this preferred conformation was over 70 fold higher than for the protein without the preferred secondary structure. Similarly, Mabs cTau7, cTau8 and cTau12 appear to recognize a secondary structure that tau assumes after cleavage. The present CNBr, epitope mapping and microtubule binding data indicate that 30 kDa to 50 kDa CSF cleaved tau proteins are comprised of the interior portion of the tau primary sequence including a functionally intact microtubule binding domain (FIGS. 3, 4 and 5).

The present data indicate that CSF levels of cleaved-tau reflect the extent of CNS axonal degeneration. CSF cleaved-tau levels were elevated 10,000 fold over control levels in patients hospitalized for CNS injury. Further, there was no overlap of CSF cleaved tau levels between acute CNS injury patients and controls. The sequelae of CNS injury is characterized by extended parenchymal atrophy and axonal degeneration (Adams et al., 1989). Microtubule-associated protein tau is a neuron-specific cytoskeletal protein localized in the axonal compartment. The present data indicate that axonal degeneration is associated with significant release of cleaved tau into CSF.

SEQUENCE LISTING

<160> NUMBER OF SEQ ID NOS: 1

<210> SEQ ID NO 1
<211> LENGTH: 441
<212> TYPE: PRT
<213> ORGANISM: human clone htau40 isoform reduced
<300> PUBLICATION INFORMATION:
<301> AUTHORS: Goedert, M.
<302> TITLE: Multiple Isoforms of Human Microtubule-Associated Protein
      Tau: Sequences and Localization in Neurofibrillary Tangles of
      Alzheimer's Disease
<303> JOURNAL: Neuron
<304> VOLUME: 3
<306> PAGES: 519-526

-continued

<307> DATE: OCT-1989

<400> SEQUENCE: 1

```
Met Ala Glu Pro Arg Gln Glu Phe Glu Val Met Glu Asp His Ala Gly
 1               5                  10                  15

Thr Tyr Gly Leu Gly Asp Arg Lys Asp Gln Gly Gly Tyr Thr Met His
                20                  25                  30

Gln Asp Gln Glu Gly Asp Thr Asp Ala Gly Leu Lys Glu Ser Pro Leu
            35                  40                  45

Gln Thr Pro Thr Glu Asp Gly Ser Glu Glu Pro Gly Ser Glu Thr Ser
        50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Ala Arg Met Val
        115                 120                 125

Ser Lys Ser Lys Asp Gly Thr Gly Ser Asp Asp Lys Lys Ala Lys Gly
    130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
        195                 200                 205

Arg Ser Arg Thr Pro Ser Leu Pro Thr Pro Pro Thr Arg Glu Pro Lys
    210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
            260                 265                 270

Gly Lys Val Gln Ile Ile Asn Lys Lys Leu Asp Leu Ser Asn Val Gln
        275                 280                 285

Ser Lys Cys Gly Ser Lys Asp Asn Ile Lys His Val Pro Gly Gly Gly
    290                 295                 300

Ser Val Gln Ile Val Tyr Lys Pro Val Asp Leu Ser Lys Val Thr Ser
305                 310                 315                 320

Lys Cys Gly Ser Leu Gly Asn Ile His His Lys Pro Gly Gly Gly Gln
                325                 330                 335

Val Glu Val Lys Ser Glu Lys Leu Asp Phe Lys Asp Arg Val Gln Ser
            340                 345                 350

Lys Ile Gly Ser Leu Asp Asn Ile Thr His Val Pro Gly Gly Gly Asn
        355                 360                 365

Lys Lys Ile Glu Thr His Lys Leu Thr Phe Arg Glu Asn Ala Lys Ala
    370                 375                 380

Lys Thr Asp His Gly Ala Glu Ile Val Tyr Lys Ser Pro Val Val Ser
385                 390                 395                 400
```

-continued

```
Gly Asp Thr Ser Pro Arg His Leu Ser Asn Val Ser Ser Thr Gly Ser
            405                 410                 415

Ile Asp Met Val Asp Ser Pro Gln Leu Ala Thr Leu Ala Asp Glu Val
            420                 425                 430

Ser Ala Ser Leu Ala Lys Gln Gly Leu
            435                 440
```

TABLE 1

CSF cleaved tau levels and demographic data for patients with CNS injury and three control groups (demyelinating disease, neurologic and normal controls).

| Diseases | CSF cleaved-Tau (ng/ml) | | | Age | | N |
|---|---|---|---|---|---|---|
| | mean | range | SD | mean | SD | |
| CNS Injury[a,b,c] | 396.96 | 2.5–2,361 | 741.58 | 47.4 | 15.2 | 11 |
| Demyelinating | 0.005 | 0–0.21 | 0.03 | 40.3 | 10.3 | 41 |
| Neurologic Controls | 0.024 | 0–0.50 | 0.10 | 52.2 | 17.5 | 38 |
| Normal Controls | 0.023 | 0–0.93 | 0.15 | 53.8 | 16.0 | 41 |

Analysis of variance of CSF tau levels for four patients groups, $p < 0.001$.
[a]CSF tau levels are significantly different from neurologic control group, $p < 0.001$.
[b]CSF tau levels are significantly different from normal control group, $p < 0.001$.
[c]CSF tau levels significantly elevated from demyelinating disease group, $p < 0.001$.

References

Adams J. H., Doyle D., Ford I., Gennarelli T. A., Graham D. I., and McLellan D. R. (1989) Diffuse axonal injury in head injury: definition, diagnosis and grading. *Histopathology* 15, 49–59.

Anderton B. H., Breinberg D., Downes M. J., Green P. J., Tomlinson B. E., Ulrich J., Wood J. N., and Kahn J. (1982) Monoclonal antibodies show that neurofibrillary tangles and neurofilaments share antigenic determinants. *Nature* 298, 84–86.

Binder L. I., Frankfurter A., and Rebhun L. I. (1985) The distribution of tau in the mammalian central nervous system. *J. Cell Biol.* 101, 1371–1378.

Bobrow M. N., Harris T. D., Shaughnessy K. J. and Litt G. J. (1989) Catalyzed reporter deposition, a novel method of signal amplification. *J. Immunol. Meth.* 125, 279–285.

Boorsma D. M. and Kalsbeek G. L. (1975) A comparative study of horseradish peroxidase conjugates prepared with a one-step and a two-step process. *J. Histochem. Cytochem.* 23, 200–207.

Caputo C. B., Wischik C., Novak M., Scott C. W., Brunner W. F., De Garcini E. M., Lo M. M. S., Norris T. E. and Salama A. I. (1992) Immunological characterization of the region of tau protein that is bound to Alzheimer paired helical filaments. *Neurobiol. Aging* 13, 267–274.

Carmel G., Mager E. M., Binder L. I. and Kuret J. (1996) The structural basis of monoclonal antibody Alz50's selectivity for Alzheimer's disease pathology. *J. Biol. Chem.* 271, 32789–32795!.

Chan S.-O. and Chiu F.-C. (1995) Cloning and developmental expression of human 66 kd neurofilament protein. *Mol. Brain Res.* 29, 177–184.

Cleveland D. W., Hwo S. Y. and Kirschner M. W. (1977) Purification of tau, a microtubule-associated protein that induces the assembly of microtubules from purified tubulin. *J. Mol. Biol.* 116, 207–225.

Couchie D. and Nunez J. (1985) Immunological characterization of microtubule-associated proteins specific for the immature brain. *FEBS Lett.* 188, 331–335.

Goedert M., Spillantini M. G., Jakes R., Rutherford D. and Crowther R. A. (1989) Multiple isoforms of human microtubule-associated protein tau: sequence and localization in neurofibrillary tangles and Alzheimer's disease. *Neuron* 3, 519–526.

Gotow T. and Tanaka J. (1994) Phosphorylation of neurofilament H subunit as related to arrangement of neurofilaments. *J. Neurosci. Res.* 37, 691–713.

Greenberg S. G., Davies P., Schein J. D. and Binder L. I. (1992) Hydrofluoric acid-treated PHFτ proteins display the same biochemical properties as normal τ. *J. Biol. Chem.* 267: 564–569.

Hayes R. L., Yang K., Whitson J. S. and Posmantur R. (1995) Cytoskeletal derangements following central nervous system injury: modulation by neurotropic gene transfection. *J. Neurotrauma* 12, 933–941.

Julien J. P., Grosveld F., Yazdanbaksh K. et al.: The structure of the human neurofilament gene (NF-L): a unique exon-intron organization in the intermediate gene family. *Biochim. Biophys. Acta* 909, 10–20.

Kohler G. and Milstein C. (1975) Continuous cultures of fused cells secreting antibody of predefined specificity. *Nature* 256, 495–497.

Kosik K. S. and Finch E. A. (1987) MAP2 and tau segregate into dendritic and axonal domains after the elaboration of morphologically distinct neurties. *J. Neurosci.* 7, 3142–3153.

Kosik K. S., Orecchio L. D., Bakalis S. and Neve R. L. (1989) Developmentally regulated expression of specific tau sequences. *Neuron* 2, 1389–1397.

Laemmli, U. K. (1970) Cleavage of structural proteins during the assembly of the head of bacteriophage T4. *Nature* 227, Lee G. and Rook S. L. (1992) Expression of tau protein in non-neuronal cells: microtubule binding and stabilization. *J. Cell Sci.* 102, 227–237.

Lees J. F., Shneidman P. S., Skuntz S. F. et al.: The structure and organization of the human heavy neurofilament subunit (NF-H) and the gene encoding it. *EMBO J.* 7, 1947–1955.

Litman P., Barg J., Rindzoonski L. and Ginsburg I. (1993) Subcellular localization of tau mRNA in differentiating neuronal culture: implications for neuronal polarity. *Neuron* 10, 627–638.

Myers M. W., Lazzarini R. A., Lee V. M. et al.: (1987) The human mid-size neurofilament subunit: a repeat protein sequence and the relationship of its gene to the intermediate filament gene family. *EMBO. J.* 6, 1617–1626.

Nukina N., Kosik K. S. and Selkoe D. J. (1987) Recognition of Alzheimer's paired helical filaments by monoclonal neurofilament antibodies is due to crossreaction with tau protein. *Proc. Natl. Acad. Sci. USA* 84, 3415–3419.

Otvos L., Feiner L., Lang E., Szendrei G. I., Goedert M. and Lee V. M. Y. (1994) Monoclonal antibody PHF-1 recognizes tau protein phosphorylated at serine residues 396 and 404 *J. Neurosci. Res.* 39, 669–673.

Schiff P. B., Fant J. and Horwitz S. B. (1979) Promotion of microtubule assembly in vitro by taxol. *Nature* !277, 665–667.

Shaw G. (1986) Neurofilaments: abundent but mysterious structures. *Bioessays* 4, 161–166.

Towbin H., Staehlin T., and Gordon J. (1979) Electrophoretic transfer of proteins from polyacrylamide gels to nitrocellulose sheets: Procedure and some applications. *Proc. Natl. Acad. Sci USA* 76, 4350–4354.

Valee R. B. (1982) A taxol-dependent procedure for the isolation of microtubules and microtubule-associated proteins (MAPs). *J. Cell Biol.* 92, 435–442.

Vincent I., Rosado M. and Davies P. (1996) Mitotic mechanisms in Alzheimer's disease?. *J. Cell Biol.* 413–425.

Wolozin B. L., Pruchnicki A., Dickson D. W., and Davies P. (1986) A novel antigen in the Alzheimer's brain. *Science* 232, 648–650.

Zelman F. P. and Dean G. E. (1996) Monoclonal antibody PHF-9 recognizes phosphorylated ser404 of tau protein and labels paired helical filaments. *J. Neurosci. Res.* 46, 90–97.

What is claimed is:

1. A method of determining the presence and extent of axonal damage in the head of a patient suspected of having suffered a neurologic trauma selected from acute cerebral vascular accident, primary hemorrhages, or primary vascular injuries, said method comprising the steps:
    (a) obtaining a sample of cerebrospinal fluid from said patient;
    (b) treating said sample of cerebrospinal fluid with at least one monoclonal antibody, said at least one monoclonal antibody having been raised against an axonally-derived tau protein of SEQ ID NO:1;
    (c) detecting the presence of said axonally-derived tau protein bound to said at least one monoclonal antibody; and
    (d) comparing the amount of said axonally-derived tau protein bound to said at least one monoclonal antibody in step (c) to control samples from the group representing a normal undamaged axon state and those representing an axonal damage state.

2. A method according to claim 1 wherein said axonally-derived tau protein is a fragment of said tau protein of SEQ ID NO:1 demonstrating an apparent molecular weight in the range of 30 kDa to 50 kDa.

3. A method according to claim 2 wherein said axonally-derived protein comprises the sequence from serine$^{199}$ to serine$^{396}$ of tau protein of SEQ ID NO: 1.

4. A method according to claim 1 wherein said presence of said axonally-derived protein bound to said at least one monoclonal antibody is detected through gel electrophoresis.

5. A method according to claim 4 wherein said axonally-derived tau protein bound to said at least one monoclonal antibody is a fragment of tau protein SEQ ID NO:1 which is detected through gel electrophoresis and which gives rise to an electrophoresis gel demonstrating multiple protein bands with apparent molecular weights from 30 kDa to 50 kDa.

6. A method according to claim 1 further comprising the measurement of said axonally derived proteins in said cerebrospinal fluid by an ELISA technique.

7. The method of claim 6 wherein the ELISA employs monoclonal antibodies recognizing tau protein of SEQ ID NO: 1 present in human cerebrospinal fluid.

8. The method of claim 6 wherein said ELISA is a tau sandwich ELISA.

9. A method of determining the presence and extent of axonal damage in the head of a patient suspected of having an acute cerebrovascular accident, said method comprising the steps of:
    (a) obtaining a sample of cerebrospinal fluid from said patient;
    (b) treating said sample of cerebrospinal fluid with at least one monoclonal antibody, said at least one monoclonal antibody having been raised against an axonally-derived tau protein of SEQ ID NO:1;
    (c) detecting the presence of said axonally-derived tau protein bound to said at least one monoclonal antibody; and
    (d) comparing the amount of said axonally-derived tau protein bound to said at least one monoclonal antibody in step (c) to control samples from the group representing a normal undamaged axon state and those representing an axonal damage state.

* * * * *